US008450111B2

(12) United States Patent
Salvo et al.

(10) Patent No.: US 8,450,111 B2
(45) Date of Patent: *May 28, 2013

(54) LIPID EXTRACTION FROM MICROALGAE USING A SINGLE IONIC LIQUID

(75) Inventors: Roberto Di Salvo, Madison, AL (US); Alton Reich, Huntsville, AL (US); H. Waite H. Dykes, Jr., Huntsville, AL (US); Rodrigo Teixeira, Huntsville, AL (US)

(73) Assignee: Streamline Automation, LLC, Huntsville, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/970,484

(22) Filed: Dec. 16, 2010
(Under 37 CFR 1.47)

(65) Prior Publication Data

US 2011/0130551 A1     Jun. 2, 2011

Related U.S. Application Data

(60) Provisional application No. 61/309,439, filed on Mar. 2, 2010.

(51) Int. Cl.
| | | |
|---|---|---|
| C12N 1/12 | (2006.01) | |
| C12N 5/00 | (2006.01) | |
| C12N 5/02 | (2006.01) | |
| C12P 1/00 | (2006.01) | |
| C12P 39/00 | (2006.01) | |

(52) U.S. Cl.
USPC ............ 435/390; 435/41; 435/42; 435/257.1; 435/383; 435/946

(58) Field of Classification Search
None
See application file for complete search history.

(56) References Cited

U.S. PATENT DOCUMENTS

| | | | |
|---|---|---|---|
| 1,943,176 A | 1/1934 | Basel | |
| 2,393,293 A | 1/1946 | Corley | |
| 3,632,330 A | 1/1972 | Michaelson | |
| 3,753,362 A | 8/1973 | Kerst | |
| 3,871,861 A | 3/1975 | Merianos | |
| 4,065,875 A | 1/1978 | Srna | |
| 4,189,311 A | 2/1980 | Laqua | |
| 4,328,118 A | 5/1982 | Friedmann | |
| 4,554,390 A | 11/1985 | Curtain | |
| 5,413,722 A | 5/1995 | Eastman | |
| 5,783,091 A | 7/1998 | Werle | |
| 5,801,050 A | 9/1998 | Uchida | |
| 5,910,254 A | 6/1999 | Guelcher | |
| 5,951,875 A | 9/1999 | Kanel | |
| 5,994,383 A | 11/1999 | Dyer | |
| 6,000,551 A | 12/1999 | Kanel | |
| 6,010,996 A | 1/2000 | Hu | |
| 6,180,376 B1 | 1/2001 | Lidell | |
| 6,291,397 B1 | 9/2001 | Wilkins | |
| 6,524,486 B2 | 2/2003 | Borodyanski | |
| 6,808,557 B2 | 10/2004 | Holbrey | |
| 6,824,599 B2 | 11/2004 | Swatloski | |
| 7,122,505 B1 | 10/2006 | Unhoch | |
| 7,662,616 B2 | 2/2010 | Hazelbeck | |
| 7,682,821 B2 | 3/2010 | Woods | |
| 7,687,261 B2 | 3/2010 | Hazlebeck | |
| 7,736,508 B2 | 6/2010 | Limcaco | |
| 7,763,457 B2 | 7/2010 | Dunlop | |
| 7,763,724 B2 | 7/2010 | Kang | |
| 7,776,211 B2 | 8/2010 | Limcaco | |
| 7,777,085 B2 | 8/2010 | Berry | |
| 7,824,904 B1 | 11/2010 | Dimanshteyn | |
| 8,211,307 B2 * | 7/2012 | Chew et al. ................... 210/634 |
| 2003/0001439 A1 | 1/2003 | Schur | |
| 2004/0040913 A1 | 3/2004 | Oberlander | |
| 2004/0144338 A1 | 7/2004 | Goldman | |
| 2005/0115893 A1 | 6/2005 | Brune | |
| 2005/0262588 A1 | 11/2005 | Dehesh | |
| 2006/0241287 A1 | 10/2006 | Hecht | |
| 2007/0048848 A1 | 3/2007 | Sears | |
| 2007/0161095 A1 | 7/2007 | Gurin | |
| 2007/0191303 A1 | 8/2007 | Dillon | |
| 2007/0196894 A1 | 8/2007 | Sim | |
| 2008/0000436 A1 | 1/2008 | Goldman | |
| 2008/0044887 A1 | 2/2008 | Maltezos | |
| 2008/0090284 A1 | 4/2008 | Hazelbeck | |
| 2008/0096267 A1 | 4/2008 | Howard | |
| 2008/0135474 A1 | 6/2008 | Limcaco | |
| 2008/0135475 A1 | 6/2008 | Limcaco | |
| 2008/0149550 A1 | 6/2008 | Suarez | |
| 2008/0155888 A1 | 7/2008 | Vick | |
| 2008/0160591 A1 | 7/2008 | Wilson | |
| 2008/0178739 A1 | 7/2008 | Lewnard | |
| 2008/0182298 A1 | 7/2008 | Day | |
| 2008/0188676 A1 | 8/2008 | Anderson | |
| 2008/0220486 A1 | 9/2008 | Weiss | |
| 2008/0220515 A1 | 9/2008 | McCall | |
| 2008/0299633 A1 | 12/2008 | Rush | |
| 2009/0011492 A1 | 1/2009 | Berzin | |
| 2009/0023180 A1 | 1/2009 | Dillon | |

(Continued)

*Primary Examiner* — Debbie K Ware
(74) *Attorney, Agent, or Firm* — KIPA AB; Tomas Friend

(57) ABSTRACT

A one-step process for the lysis of microalgae cell walls and separation of the cellular lipids for use in biofuel production by utilizing a hydrophilic ionic liquid, 1-butyl-3-methylimidazolium. The hydrophilic ionic liquid both lyses the microalgae cell walls and forms two immiscible layers, one of which consists of the lipid contents of the lysed cells. After mixture of the hydrophilic ionic liquid with a suspension of microalgae cells, gravity causes a hydrophobic lipid phase to move to a top phase where it is removed from the mixture and purified. The hydrophilic ionic liquid is recycled to lyse new microalgae suspensions.

18 Claims, 6 Drawing Sheets

U.S. PATENT DOCUMENTS

| | | |
|---|---|---|
| 2009/0029445 A1 | 1/2009 | Eckelberry |
| 2009/0047721 A1 | 2/2009 | Trimbur |
| 2009/0056201 A1 | 3/2009 | Morgan |
| 2009/0071064 A1 | 3/2009 | Machacek |
| 2009/0077864 A1 | 3/2009 | Marker et al. |
| 2009/0081742 A1 | 3/2009 | Dunlop |
| 2009/0119980 A1 | 5/2009 | Walker |
| 2009/0130706 A1 | 5/2009 | Berzin |
| 2009/0151240 A1 | 6/2009 | Kayama |
| 2009/0181440 A1 | 7/2009 | Rush |
| 2009/0203116 A1 | 8/2009 | Bazaire |
| 2009/0230040 A1 | 9/2009 | Limcaco |
| 2009/0234146 A1 | 9/2009 | Cooney |
| 2009/0291490 A1 | 11/2009 | Spradling |
| 2009/0298158 A1 | 12/2009 | Thomas |
| 2009/0298159 A1 | 12/2009 | Wu |
| 2009/0301399 A1 | 12/2009 | Brown et al. |
| 2009/0314193 A1 | 12/2009 | Groves et al. |
| 2009/0317901 A1 | 12/2009 | Vance |
| 2010/0003739 A1 | 1/2010 | Duhring |
| 2010/0050502 A1 | 3/2010 | Wu |
| 2010/0055765 A1 | 3/2010 | Frank |
| 2010/0068776 A1 | 3/2010 | Woods |
| 2010/0068801 A1 | 3/2010 | Woods |
| 2010/0077654 A1 | 4/2010 | Wu |
| 2010/0081835 A1 | 4/2010 | Wu |
| 2010/0093078 A1 | 4/2010 | Wang |
| 2010/0144017 A1 | 6/2010 | Shepherd |
| 2010/0151539 A1 | 6/2010 | Franklin |
| 2010/0151540 A1 | 6/2010 | Gordon |
| 2010/0151558 A1 | 6/2010 | Alianell |
| 2010/0159578 A1 | 6/2010 | Lacaze |
| 2010/0170144 A1 | 7/2010 | Day |
| 2010/0170150 A1 | 7/2010 | Walsh, Jr. |
| 2010/0196742 A1 | 8/2010 | Nealson et al. |
| 2010/0196967 A1 | 8/2010 | Edye |
| 2010/0227368 A1 | 9/2010 | Steiner |
| 2010/0233761 A1 | 9/2010 | Czartoski |
| 2010/0233787 A1 | 9/2010 | Katchanov |
| 2010/0236137 A1 | 9/2010 | Wu |
| 2010/0248333 A1 | 9/2010 | Bartison |
| 2010/0257781 A1 | 10/2010 | Batty et al. |
| 2010/0260618 A1 | 10/2010 | Parsheh |
| 2010/0267122 A1 | 10/2010 | Chinnasamy |
| 2010/0269514 A1 | 10/2010 | Fulton, III |
| 2010/0276361 A1 | 11/2010 | Limcaco |
| 2010/0285576 A1 | 11/2010 | Norbeck |

* cited by examiner

LIPID EXTRACTION FROM MICROALGAE USING A SINGLE IONIC LIQUID

This application claims the benefit of filing priority under 35 U.S.C. §119 and 37 C.F.R. §1.78 from U.S. Provisional Application Ser. No. 61/309,439 filed Mar. 2, 2010, for LIPID EXTRACTION FROM MICROALGAE USING A SINGLE IONIC LIQUID. All information disclosed in this prior application is incorporated herein by reference.

STATEMENT REGARDING FEDERALLY SPONSORED RESEARCH OR DEVELOPMENT

The United States Government has certain rights to the disclosed invention pursuant to Contract Number DE-SC0001306 awarded by the U.S. Department of Energy.

FIELD OF THE INVENTION

The present invention relates to methods, compositions, and apparatus used to extract lipids and other products from microalgae using a single ionic liquid and requiring no co-solvents.

BACKGROUND OF THE INVENTION

Biofuel production via microalgal systems can produce a wide range of feedstocks for transformation into biodiesel, bioethanol, biomethane and biohydrogen (FIG. 1). Microalgae can be cultivated in non-food producing environments such as deserts and oceans and may utilize fresh, saline or waste water streams in conjunction with $CO_2$-producing power and industrial plants for fixing carbon and reutilizing phosphates and nitrates.

Lipid molecules are stored inside small spherical structures inside microalgal cells called vesicles. In order to access the contents of the vesicles the cell wall must be disturbed or lysed. Disruption creates holes in the cell wall, resulting in the partial release of contents. Lysis results in the complete release of contents.

Consequently, complete or nearly complete destruction or removal of the cell wall is critical. Microalgal cell walls contain cellulose, which make their complete lysis by organic solvents alone difficult or impossible. In addition, vesicle walls are made of lipid mono-lbilayers, which must also be disrupted or lysed, but are susceptible to chemical lysis by organic solvents and aqueous detergents. Because chemical lysis requires costly and/or toxic chemicals that must be separated from the desired products, cell concentrates are usually lysed nonchemically using one or more of high-pressure homogenization, supercritical fluid homogenization, electroporation, and radiation, all of which are energy-intensive because of the dissipative effects of the intervening aqueous media. Lipids are then usually removed from the cell lysate via distillation.

Current methods for harvesting microalgae and extracting biofuels and other lipids from the harvested microalgae also involve one or more processes that concentrate algae cells. Microalgae cell concentration is often inefficient because the cells possess physical properties that are similar to the suspending aqueous medium, including similar density, magnetic susceptibility, and refractive index.

SUMMARY OF THE INVENTION

The present invention results, in part, from the unexpected discovery that cell lysis and separation of lipids from the cell lysate can be performed in a single step using a single, hydrophilic ionic liquid that can dissolve the cellulose cell wall matrix of microalgae cells (FIG. 2). Normally, cell lysis and extraction by chemical means involves the use of two immiscible solvent phases with one solvent being hydrophilic for dissolving water soluble molecules from the cell lysate and the other solvent being hydrophobic to dissolve lipids and other lipophilic molecules from the cell lysate. While investigating hydrophilic ionic liquids for their ability to dissolve low concentrations of cellulose, which compose about 1% by mass of the whole cell, the inventor unexpectedly discovered that certain hydrophilic ionic liquids capable of dissolving cellulose from plant material are also capable of completely lysing microalgae cell walls and microalgae vesicle membranes to form two immiscible layers, one of which consists of the lipid contents of the lysed cells.

The lysis and separation step initially results in lipid vesicles and cell debris suspended in a hydrophilic ionic liquid medium and, through the force of gravity, finally results in a hydrophobic lipid phase resting on an immiscible, lower hydrophilic ionic liquid phase. The upper lipid layer may easily be removed from the ionic liquid and processed. Also, because the ionic liquid has almost zero vapor pressure, lipids having lower boiling points than water may be alternatively be recovered from the cell lysate using a simple "single-tray" distillation with gentle heating. This may be followed by removal of water and further distillation of lipids from the lysate.

The ionic liquid may then be conveniently recycled to lyse more microalgae. While ionic liquids capable of dissolving cellulose are known, these ionic liquids have been used with co-solvents for the extraction of cellulose and other materials from biological source material. The present invention provides for a simplified method for effectively extracting desired materials from biological source materials such as cells using a single ionic liquid to both lyse cells and to form two immiscible layers, one of which contains lipids from the cell lysate.

DETAILED DESCRIPTION OF THE DRAWINGS

DETAILED DESCRIPTION OF THE INVENTION

Figure 1:
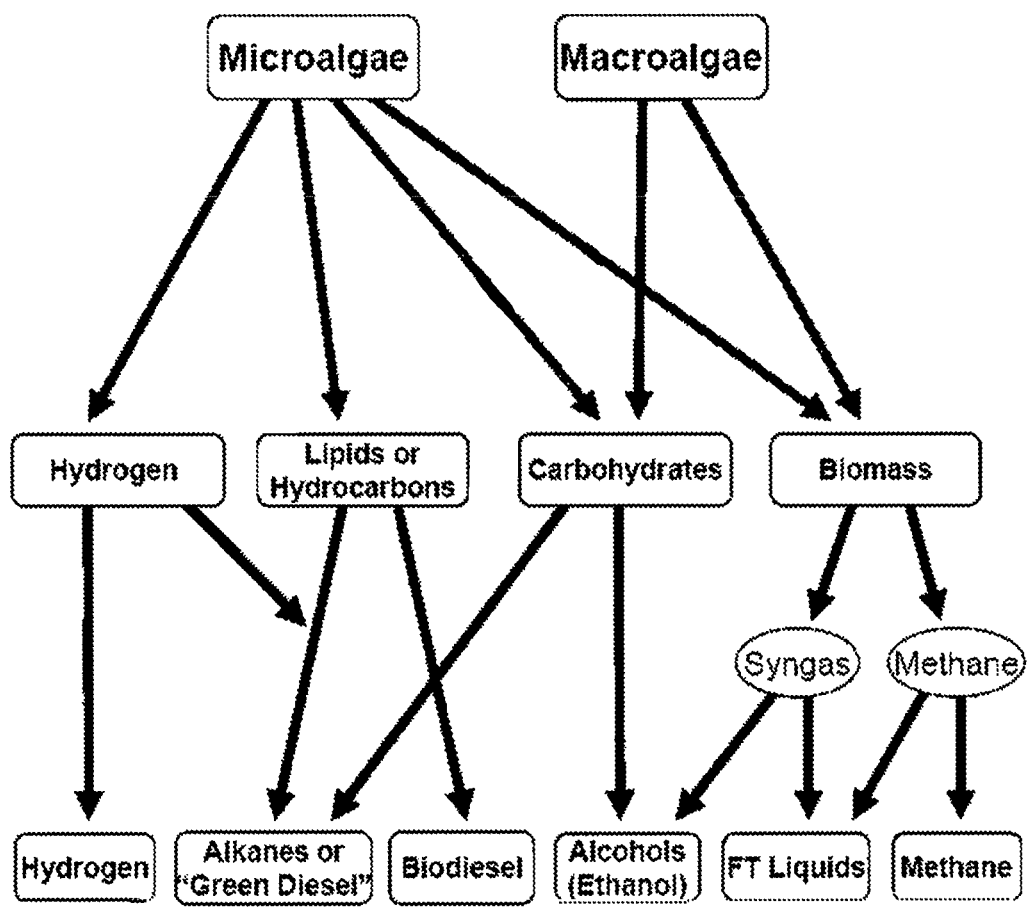
FIG. 1 depicts a range of algae feedstocks for transformation into biodiesel, bioethanol, biomethane and biohydrogen.
Figure 2:
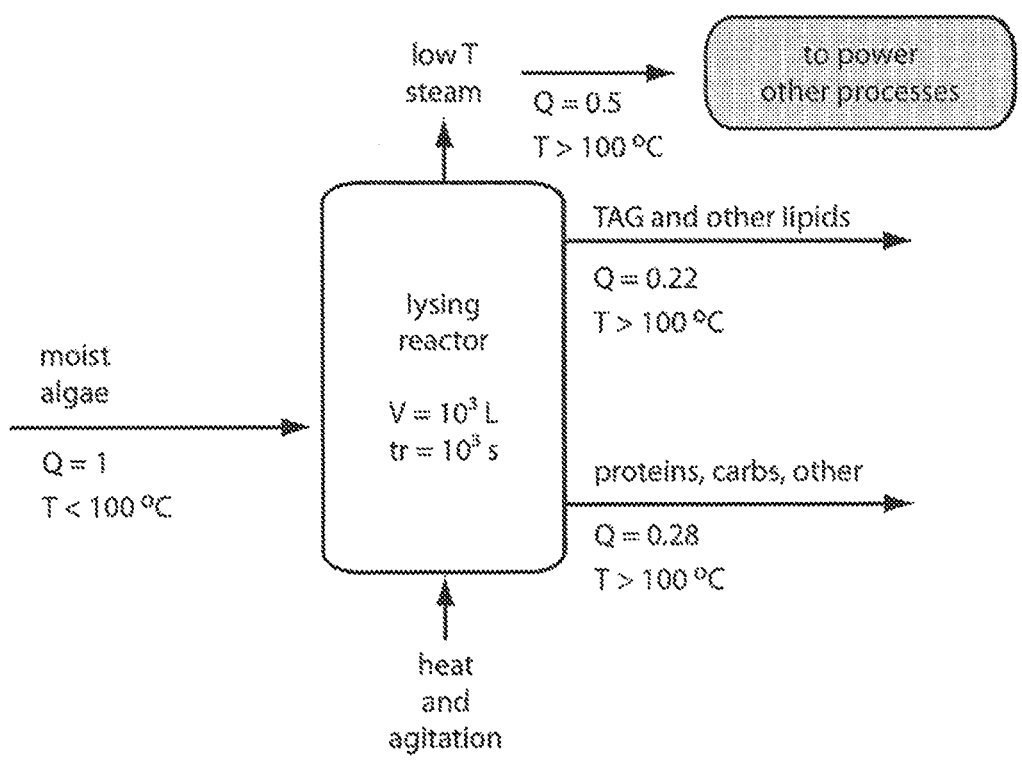
FIG. 2 depicts a system for algae cell lysis and separation of lipids from the cell lysate in accordance with a preferred embodiment of the present invention.
Figure 3:
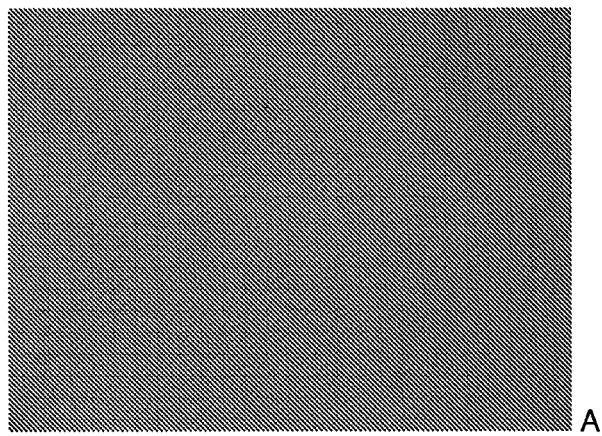
FIG. 3 depicts sample results of experiments in which three 1-butyl-3-methylimidazolium (BMIM) ionic liquids were tested for their ability to lyse aqueous suspensions of *Chlorella pyrenoidosa* in accordance with a preferred embodiment of the present invention.
Figure 3:
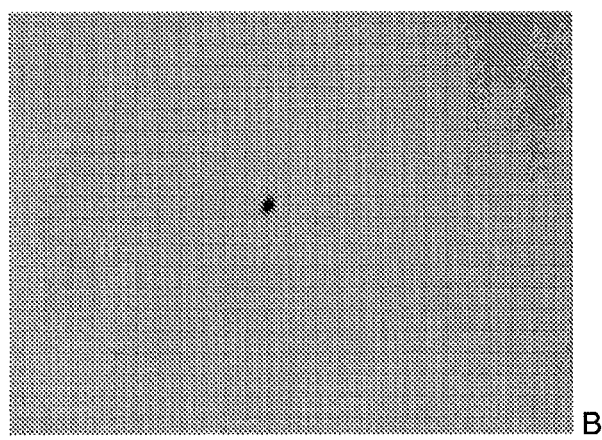
Figure 3:
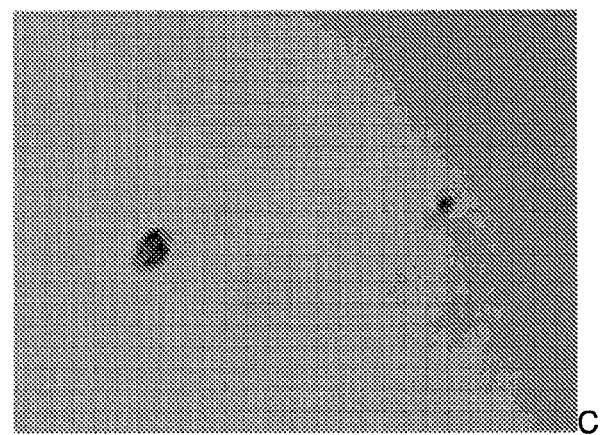

FIG. 3 shows sample results of experiments in which three 1-butyl-3-methylimidazolium (BMIM) ionic liquids were tested for their ability to lyse aqueous suspensions of *Chlorella pyrenoidosa* (*C. pyren.*), a lipid-producing freshwater microalgae. All reactions were carried out at temperatures of between 50° C. and 140° C. with mixing, but temperatures above 100° C. were necessary to improve mixing and evaporate water quickly in order to lower the lysing reaction duration to 10-30 minutes. Of the three ILs, only [BMIM]Cl is capable of rapidly and completely lysing aqueous suspensions of *C. pyren.*

Figure 4:
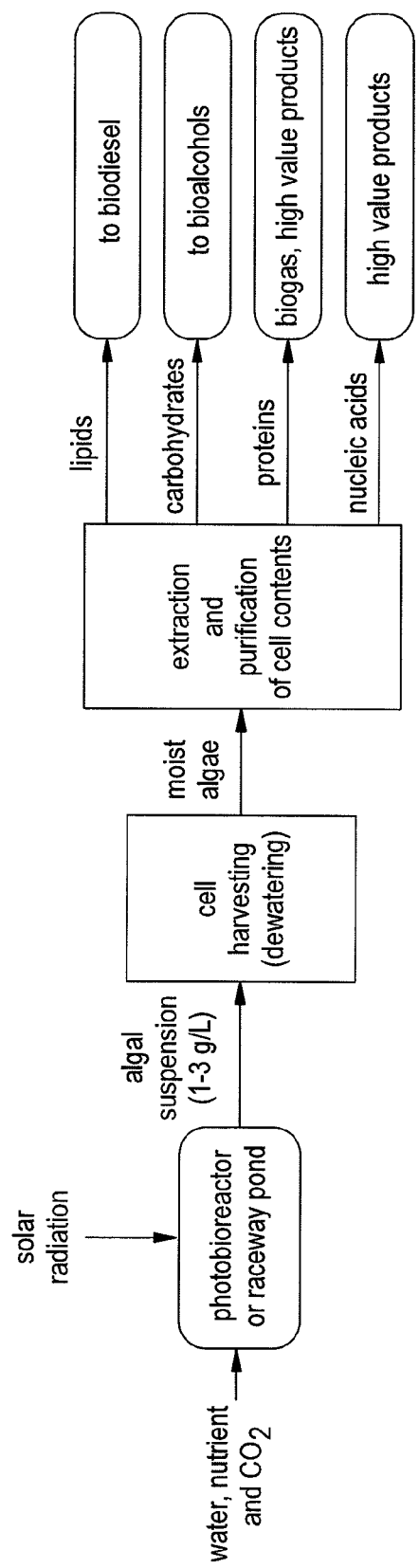
FIG. 4 depicts processing steps for extracting triacylglycerols (TAG) and other lipids for production of biofuels from a microalgae cell suspension in accordance with a preferred embodiment of the present invention.

FIG. 4 illustrates processing steps for extracting triacylglycerols (TAG) and other lipids for production of biofuels and other products from a microalgae cell suspension. An initial algae cell suspension containing, for example, 1-3 grams per liter microalgae cells is dewatered to produce a more concentrated suspension (moist algae) containing between 0.1 and 1 kilogram of microalgae cells per liter. The concentrated suspension is introduced into a reaction vessel containing ionic liquid maintained at a temperature of between 100° C. and 110° C., preferably at or below 105° C. and at ambient, atmospheric pressure. The ionic liquid lyses the microalgae cells and, because the ionic liquid is immiscible with and more dense than lipids in the cell lysate, triacylglycerols and other lipids separate from the ionic liquid to form a lipid layer over the ionic liquid. Other components of the cell lysate such as celluloses, carbohydrates, proteins, and nucleic aids may also be separated from the ionic liquid by a method such as conventional liquid-liquid extraction and purified. Lipids having boiling points near the temperature of the ionic liquid are volatilized in the reaction vessel and may be recovered and/or purified by condensation using a condenser configured to receive vapor generated in the reaction vessel.

Lysis and separation may be performed continuously in the reaction vessel by causing mixing to occur in a specific zone within the vessel where lysis occurs continuously. The contents of the cell lysate continuously move out of the mixing zone into regions within the vessel in which the ionic liquid is undisturbed and separate according to specific gravity. Mixing within the mixing zone may be driven by mechanical means or by injecting the microalgae cell suspension through nozzles and/or at flow velocities that induce mixing with the ionic liquid.

Figure 5:
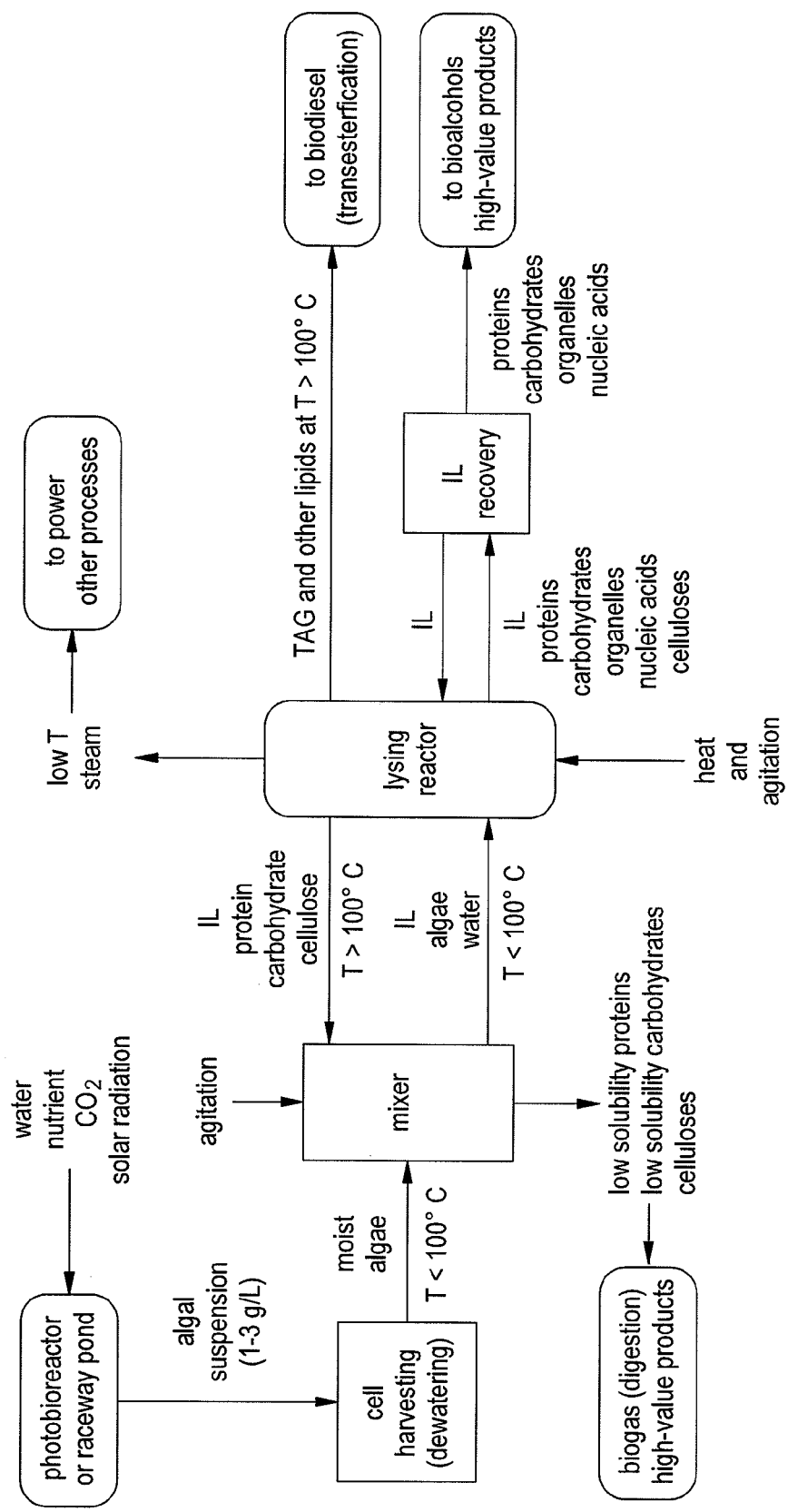
FIG. 5 depicts a lipid extraction process in which ionic liquid is recirculated between the reaction vessel (lysing reactor) and a mixing vessel and between the reaction vessel and an ionic liquid recovery vessel in accordance with a preferred embodiment of the present invention.

FIG. 5 shows a lipid extraction process in which ionic liquid is recirculated between the reaction vessel (lysing reactor) and a mixing vessel and between the reaction vessel and an ionic liquid recovery vessel. Concentrated algae cell suspension is fed into the mixing vessel in which ionic liquid is maintained at a temperature of less than 100° C. Ionic liquid entering the mixing vessel from the reaction vessel is cooled and is diluted by the relatively higher water content in the mixing vessel than the reaction vessel. The simultaneous cooling and dilution of the ionic liquid causes cellulose and other low solubility species to precipitate. The concentrated algae suspension is preheated by ionic liquid from the reaction vessel and is fed into the reaction vessel, which is maintained at a temperature of 100° C. or higher. In the reaction vessel, water and other species having boiling points of 100° C. or lower are driven from the ionic liquid. This facilitates the lysis of the incoming algae cells because the amount of cell suspension that can be lysed is limited by the water content of the ionic liquid algae suspension mixture. Droplets containing TAGs and other lipids from the cell lysate rise to the top of the IL where they form a separate phase and, for example, can be transferred to a reactor for transesterification into biodiesel at an optimal temperature. IL is also fed into a recovery vessel that removes soluble proteins, carbohydrates, nucleic acids and other macromolecules to regenerate clean IL. The macromolecules removed from the IL may be fed directly into purification processes to produce other high value products such as food supplements and synthetic precursors for drugs.

Figure 6:
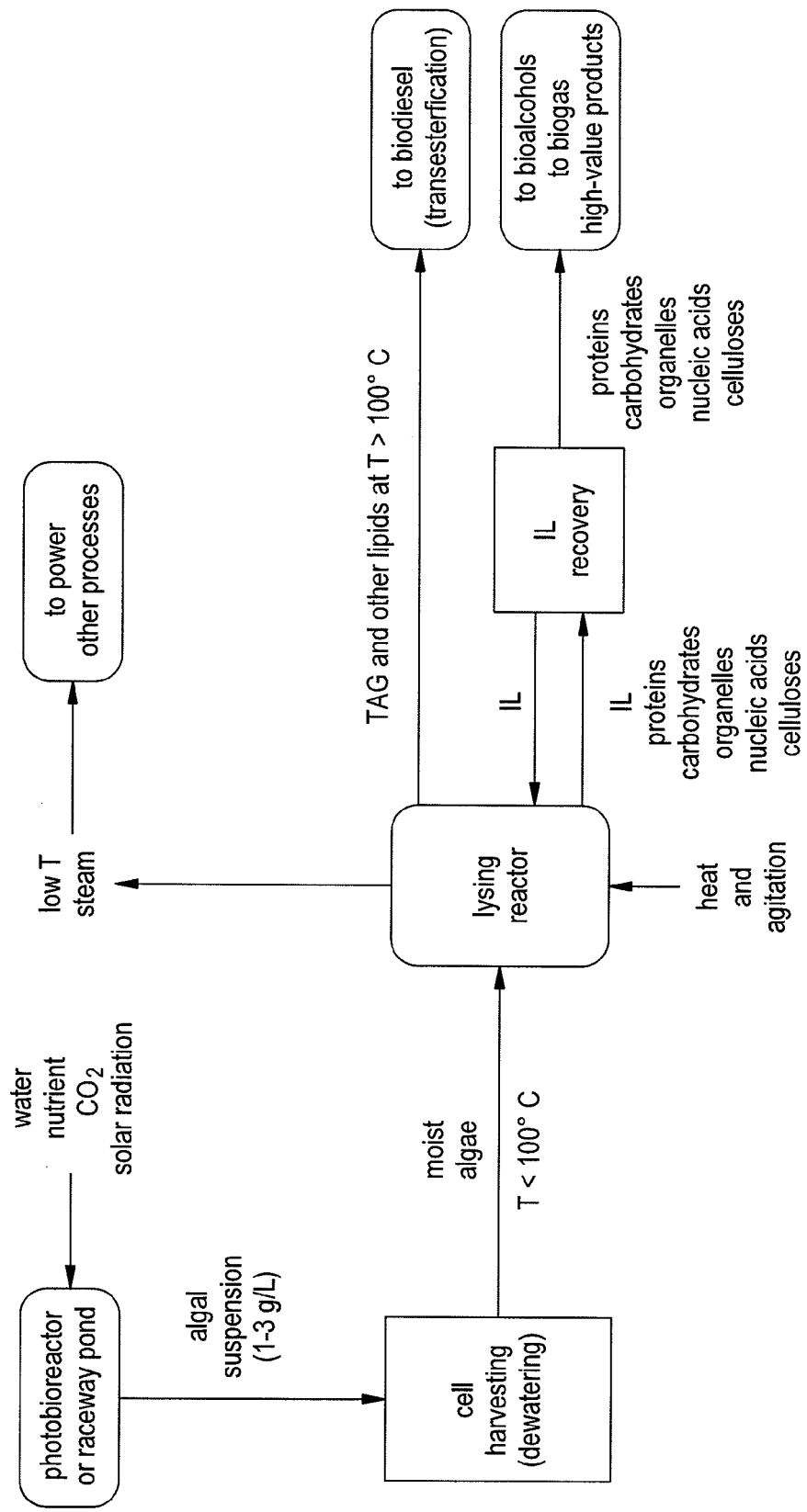
FIG. 6 shows a lipid extraction process analogous to that shown in FIG. 5, but using direct loading of harvested cells.

FIG. 6 shows a lipid extraction process analogous to that shown in FIG. 5, but using direct loading of harvested cells. Dilute algal cell suspension is harvested (dewatered) and fed directly into the reaction vessel at a temperature of less than 100° C. The temperature within the reaction vessel is then raised to over 100° C., driving off water and facilitating cell lysis.

What is claimed is:

1. A method for extracting a lipid from a suspension of microalgae cells comprising the steps of:
    a) mixing an amount of said suspension of microalgae cells with an amount of 1-butyl-3-methylimidazolium chloride at a temperature of between 100° C. and 140° C. for a time sufficient to lyse said microalgae cells to produce a lysate;
    b) allowing the lysate to rest for a time sufficient for water to evaporate from the lysate and for the lysate to form a hydrophilic phase comprising the 1-butyl-3-methylimidazolium chloride and a lipid phase separate from and immiscible with the hydrophilic phase, said lipid phase having a lower density than the hydrophilic phase; and
    c) separating the lipid phase from the hydrophilic phase to obtain a lipid extract from the microalgae cells.

2. The method of claim 1, and further comprising the step of removing water from the suspension of microalgae before step a) by causing microalgae cells to sediment and removing water from above the sedimented cells.

3. The method of claim 1, and further comprising the step of removing water from the suspension of microalgae before step a) by filtration and/or centrifugation.

4. The method of claim 1, and further comprising repeating steps a) through c) using the same 1-butyl-3-methylimidazolium chloride.

5. The method of claim 1, and further comprising the step of separating lipids within the lipid phase from one another.

6. The method of claim 1, wherein the microalgae cells are freshwater or saltwater microalgae cells.

7. The method of claim 6, wherein the microalgae cells are *Chlorella pyreniodosa*.

8. The method of claim 1, wherein the suspension of microalgae cells comprises 5% to 100% cells by weight of the cell suspension.

9. The method of claim 8, wherein the suspension of microalgae cells and 1-butyl-3-methylimidazolium chloride, at the beginning of mixing in step a) are present in a weight ratio of 1 to 20.

10. The method of claim 1, wherein the temperature of mixing in step a) is between 105° C. and 110° C.

11. The method of claim 1, wherein the lipid extract comprises a triacylglycerol.

12. The method of claim 1, and further comprising the method step
    d) separating celluloses, carbohydrates, proteins and/or nucleic acids from the hydrophilic phase to regenerate clean ionic liquid and obtain substrates and precursors for the production of biofuels, food supplements and drugs.

13. A continuous method for extracting a lipid from a suspension of microalgae cells comprising the steps of:
    a) flowing a suspension of microalgae cells into a reactor vessel containing 1-butyl-3-methylimidazolium chloride maintained at a temperature of between 100° C. and 140° C.;
    b) mixing the suspension of microalgae cells with said 1-butyl-3-methylimidazolium chloride within a predetermined zone of the reactor vessel to produce a microalgae cell lysate, such that a lipid in said cell lysate migrates to form a top phase that is immiscible with said 1-butyl-3-methylimidazolium chloride and water from the cell lysate;

c) allowing said lysate to rest for a time sufficient for water to evaporate from the lysate to form a hydrophilic phase comprising the 1-butyl-3-methylimidazolium chloride and a lipid phase separate from and immiscible with the hydrophilic phase; and d) separating the lipid phase from the hydrophilic phase to obtain a lipid extract from the microalgae cells.

14. The method of claim 13, and further comprising the method step e) separating celluloses, carbohydrates, proteins, nucleic acids and/or other macromolecules from the hydrophilic phase to regenerate clean ionic liquid.

15. A method for extracting a component of microalgae cells, comprising:

contacting the microalgae cells with a solvent consisting essentially of 1-butyl-3-methylimidazolium chloride, mixing the microalgae cells and the solvent, and causing a multiple-phase composition to form, wherein a first phase of the multiple-phase composition includes a microalgae cell component that is immiscible with the solvent wherein the contacting and the mixing of the microalgae cells and the solvent occurs at a temperature between about 105° C. and about 110° C.

16. The method according to claim 15, and further comprising removing the microalgae cell component from the multiple-phase composition.

17. The method according to claim 16, wherein the microalgae cell component includes a lipid or multiple lipids.

18. The method according to claim 17, wherein the lipid is a triacylglycerol.

* * * * *

UNITED STATES PATENT AND TRADEMARK OFFICE
CERTIFICATE OF CORRECTION

PATENT NO. : 8,450,111 B2  
APPLICATION NO. : 12/970484  
DATED : May 28, 2013  
INVENTOR(S) : Robert Di Salvo et al.

Page 1 of 1

It is certified that error appears in the above-identified patent and that said Letters Patent is hereby corrected as shown below:

Title Page, Item (12) "Salvo et al." should read --Di Salvo et al.--.

In the Specification  
Column 3, line 4, ""°C." (first and second occurrence) should read --°C--.  
Column 3, line 5, ""°C." should read --°C--.  
Column 3, line 18, ""°C." should read --°C--.  
Column 3, line 19, ""°C." (first and second occurrence) should read --°C--.  
Column 3, line 55, ""°C." should read --°C--.  
Column 3, line 57, ""°C." should read --°C--.

In the Claims  
Column 4, line 8, ""°C." should read --°C--.  
Column 4, line 15, ""°C." (first and second occurrence) should read --°C--.  
Column 4, line 50, ""°C." (first and second occurrence) should read --°C--.  
Column 4, line 64, ""°C." should read --°C--.  
Column 4, line 65, ""°C." should read --°C--.  
Column 6, line 10, ""°C." (first and second occurrence) should read --°C--.

Signed and Sealed this  
Twenty-sixth Day of November, 2013

Margaret A. Focarino  
*Commissioner for Patents of the United States Patent and Trademark Office*